(12) United States Patent
Pidaparti et al.

(10) Patent No.: US 9,988,647 B2
(45) Date of Patent: Jun. 5, 2018

(54) METHODS OF ANAEROBIC DIGESTION OF BIOMASS TO PRODUCE BIOGAS

(71) Applicant: Novus Energy, LLC, Minneapolis, MN (US)

(72) Inventors: Surya Raja Pidaparti, Maple Grove, MN (US); Jeffrey Ray Zierdt, Monticello, MN (US); Joseph Philip Burke, Edina, MN (US)

(73) Assignee: Viresco AD, LLC, Ridgefield, CT (US)

( * ) Notice: Subject to any disclaimer, the term of this patent is extended or adjusted under 35 U.S.C. 154(b) by 0 days. days.

(21) Appl. No.: 15/338,415

(22) Filed: Oct. 30, 2016

(65) Prior Publication Data
US 2017/0044574 A1 Feb. 16, 2017

Related U.S. Application Data

(62) Division of application No. 14/027,121, filed on Sep. 13, 2013, now Pat. No. 9,523,102.

(60) Provisional application No. 61/700,743, filed on Sep. 13, 2012.

(51) Int. Cl.
| | |
|---|---|
| *C12P 1/04* | (2006.01) |
| *C12P 5/02* | (2006.01) |
| *C12M 1/107* | (2006.01) |
| *C12M 1/00* | (2006.01) |
| *C12M 1/12* | (2006.01) |
| *C12M 1/36* | (2006.01) |
| *C12M 1/34* | (2006.01) |
| *C12M 1/33* | (2006.01) |

(52) U.S. Cl.
CPC ............. *C12P 5/023* (2013.01); *C12M 21/04* (2013.01); *C12M 23/36* (2013.01); *C12M 23/52* (2013.01); *C12M 25/16* (2013.01); *C12M 29/00* (2013.01); *C12M 41/00* (2013.01); *C12M 41/28* (2013.01); *C12M 41/48* (2013.01); *C12M 45/02* (2013.01); *C12M 45/04* (2013.01); *C12M 45/06* (2013.01); *Y02E 50/343* (2013.01)

(58) Field of Classification Search
CPC .................................. C12P 1/04; C12M 21/04
See application file for complete search history.

(56) References Cited

U.S. PATENT DOCUMENTS

2011/0151533 A1* 6/2011 Downey ................ C12M 21/04
435/167

* cited by examiner

*Primary Examiner* — Ruth A Davis
(74) *Attorney, Agent, or Firm* — Hugh McTavish

(57) ABSTRACT

Improved methods for anaerobic digestion of organic matter to produce biogas. Among the improvements given are including ferric iron in a hydrolysis reactor to increase the rate and efficiency of anaerobic hydrolysis to provide substrates for methanogenesis. A solids separation step is added after hydrolysis and before methanogenesis to improve the efficiency of the methanogenesis step. Other improvements involve using separate tanks for the hydrolysis and methanogenesis stages and using two (or more) methanogenesis tanks in sequence, and switching the order of the two (or more) methanogenesis tanks periodically.

17 Claims, 6 Drawing Sheets

METHODS OF ANAEROBIC DIGESTION OF BIOMASS TO PRODUCE BIOGAS

BACKGROUND

Anaerobic Digestion (AD) is a way of converting organic biomass to biogas. Hazardous chemical waste can also often be digested by microorganisms and disposed of by fermentation.

AD produces biogas, a mixture of primarily methane and carbon dioxide, which can be used for energy. This is an advantage over landfilling waste.

AD has three distinct phases: hydrolysis, acetogenesis and methanogenesis. Hydrolysis and acetogenesis often occur in the same tank and are thus sometimes considered one phase.

In AD, anaerobic microorganisms ferment carbon substrates to products in the absence of oxygen or oxygen surrogates. For instance, some organisms transform hexose sugars to ethanol and $CO_2$. Other common fermentation products include lactic acid, acetic acid, butyric acid, $H_2$, and methane. Many of these compounds are themselves substrates for further anaerobic metabolism by other microorganisms. However, two fermentation products cannot be further fermented—methane and $CO_2$. Thus, all anaerobic decomposition can ultimately lead to methane and carbon dioxide.

AD biologically is generally considered to occur in two phases: (1) Breakdown of sugars and carbohydrates to smaller molecules, particularly organic acids such as acetic acid and butyric acid. This is known as hydrolysis or sometimes as acid production. And (2) production of methane and $CO_2$ from the smaller organic molecules produced in phase (1), known as methanogenesis. Different organisms catalyze phases (1) and (2). Acid forming microorganisms and other microrganisms, that include both facultative and obligate anaerobic microorganisms catalyze phase (1), the hydrolysis phase. Organisms that produce methane are called methanogens. Methanogens can produce methane from acetate by the reaction acetate+$H_2O \rightarrow$ methane+$HCO_3^-$. Methanogens can also produce methane from hydrogen and $CO_2$ by the reaction $4H_2+HCO_3^-+H^+\rightarrow CH_4+3H_2O$. The hydrogen for methanogenesis from carbon dioxide in nature comes from fermentation of reduced carbon substrates. Only methanogens—which are obligate anaerobes—produce methane, hydrogen and carbon dioxide through the cleaving of acetate and formate and remove protons from the cytoplasm.

Methanogenesis is the most essential part of AD as it is the only stage that removes protons from the cytoplasm to allow the preceding steps to proceed. A well-functioning methanogenesis stage is key to maintaining a functional and efficient AD systems. Without it AD systems become septic and fail.

Of all metabolic pathways, methanogenesis yields the least amount of energy as the end product—methane—has a high enthalpy. Consequently there is minimal energy yield for the organisms involved causing them to grow very slowly. System design to retain biomass is critical. Traditional AD systems accomplish stability through large tanks that provide adequate time for a stable methanogen population to be maintained. This results in large tanks that are expensive to build and are not optimum.

Even in such tanks the process is always somewhat incomplete: some portion of the substrate is not digested all the way to methane and $CO_2$. And the speed of the process is a limiting factor that determines the size of reactors needed. Thus, more efficient and faster methods of anaerobic digestion are needed, and digester systems that facilitate or allow more efficient and faster anaerobic digestion are needed.

SUMMARY

The inventors have developed improved methods of fermentation that ferment organic substrates to biogas more quickly and more completely than typical current methods.

One embodiment provides a method of producing biogas comprising:

(a)(i) grinding an organic substrate comprising solids to produce smaller solids particles (thus allowing for more intimate contact of the substrate with the microorganisms);

(a)(ii) transferring the substrate with smaller solids particles to a hydrolysis tank;

(a)(iii) hydrolyzing the substrate in an anaerobic condition in a hydrolysis tank comprising $Fe^{3+}$ particles;

(a)(iv) transferring effluent from the hydrolysis tank to a solids separator (a)(v) separating solids from the hydrolysis effluent to produce a solids fraction and a screened hydrolysis effluent;

(b)(i) transferring the screened hydrolysis effluent for a period of time 1 to a methanogenesis tank 1 comprising fixed film methanogens or granular methanogens and producing biogas and methanogenesis tank 1 liquid effluent;

(b)(ii) transferring the methanogenesis tank 1 liquid effluent to a methanogenesis tank 2 comprising fixed film methanogens or granular methanogens during period of time 1 and producing biogas and methanogenesis tank 2 liquid effluent in methanogenesis tank 2;

(b)(iii) discharging methanogenesis tank 2 liquid effluent during period of time 1;

(c) and then switching the order of methanogenesis tanks 1 and 2 and (c)(i) transferring the screened hydrolysis effluent for a period of time 2 to said methanogenesis tank 2 and producing biogas and methanogenesis tank 2 liquid effluent;

(c)(ii) transferring the methanogenesis tank 2 liquid effluent to said methanogenesis tank 1 during period of time 2 and producing biogas and methanogenesis tank 1 liquid effluent in methanogenesis tank 1;

(c)(iii) discharging methanogenesis tank 1 liquid effluent during period of time 2.

In this embodiment, ferric iron is included in the hydrolysis tank. Typically it is fed daily to the hydrolysis tank. We have found that the presence of $Fe^{3+}$ particles increases the rate and efficiency of the hydrolysis stage, broadly defined as producing substrates for methanogenesis, which may include sugars, organic acids, $H_2$, and other organic molecules and inorganic molecules that are substrates for methanogenesis. The ferric iron functions as an electron sink or electron acceptor. Other metallic electron acceptors may be used in place of ferric iron.

The above embodiment also includes a solids separation step after the hydrolysis step to produce a screened hydrolysis effluent that we have found is more suitable for the methanogenesis stage. We have found that this also improves the speed and efficiency of the methanogenesis step. The term "screened" hydrolysis effluent is used to mean that it is depleted in solids and particles as compared to the hydrolysis effluent before the solids separator. The screened hydrolysis effluent may not be totally clear or totally free of solids and particles.

It further includes using separate tanks for the hydrolysis and methanogenesis stages and using two (or more) methanogenesis tanks in sequence, and switching the order of the two (or more) methanogenesis tanks periodically. This is also found to improve the speed and efficiency of the process.

Another embodiment provides a method of producing biogas comprising:
(a)(i) transferring an organic substrate to a hydrolysis tank;
(a)(ii) hydrolyzing the substrate in anaerobic condition in a hydrolysis tank to produce a hydrolysis liquid effluent;
(b)(i) transferring the hydrolysis effluent for a period of time 1 to a methanogenesis tank 1 comprising fixed film methanogens or granular methanogens and producing biogas and methanogenesis tank 1 liquid effluent;
(b)(ii) transferring the methanogenesis tank 1 liquid effluent to a methanogenesis tank 2 comprising fixed film methanogens or granular methanogens during period of time 1 and producing biogas and methanogenesis tank 2 liquid effluent in methanogenesis tank 2;
(b)(iii) discharging methanogenesis tank 2 liquid effluent during period of time 1;
(c) and then switching the order of methanogenesis tanks 1 and 2 and
(c)(i) transferring the hydrolysis effluent for a period of time 2 to said methanogenesis tank 2 and producing biogas and methanogenesis tank 2 liquid effluent;
(c)(ii) transferring the methanogenesis tank 2 liquid effluent to said methanogenesis tank 1 during period of time 2 and producing biogas and methanogenesis tank 1 liquid effluent in methanogenesis tank 1;
(c)(iii) discharging methanogenesis tank 1 liquid effluent during period of time 2;
(d) passing the biogas produced in methanogenesis tanks 1 and 2 through a foam trap to trap foam and separate it from the biogas; and
(e) collecting the biogas downstream of the foam trap.

The biogas is collected from both methanogenesis tanks 1 and 2. It is ordinarily collected from the dome of the tanks, allowing the gas to pass through a foam trap prior to the pressure equalizing tanks in preparation for gas conditioning.

The process of anaerobic digestion often produces surfactants that cause foam to form. Foam in the biogas often causes many problems including corrosion and plugging of downstream gas units, especially when foam and vapor condenses at cooler temperatures. Including the foam trap in the process minimizes or eliminates these problems.

Another embodiment provides a method of producing biogas comprising:
(a)(i) transferring an organic substrate to a hydrolysis tank;
(a)(ii) hydrolyzing the substrate in anaerobic condition in a hydrolysis tank to produce a hydrolysis liquid effluent;
(b)(i) transferring the hydrolysis effluent for a period of time 1 to a methanogenesis tank 1 comprising fixed film methanogens or granular methanogens and producing biogas and methanogenesis tank 1 liquid effluent;
(b)(ii) transferring biogas from the methanogenesis tank 1 through a foam trap to trap foam and separate it from the biogas; and
(c) collecting the biogas downstream of the foam trap.

Another embodiment provides a method of producing biogas comprising:
(a)(i) transferring an organic substrate to a hydrolysis tank;
(a)(ii) hydrolyzing the substrate in anaerobic condition in a hydrolysis tank to produce a hydrolysis liquid effluent;
(b)(i) transferring the hydrolysis effluent for a period of time 1 to a methanogenesis tank 1 comprising granulated and fixed film methanogens and producing biogas and methanogenesis tank 1 liquid effluent;
(b)(ii) recycling liquid in methanogenesis tank 1 to promote growth of granulated and attached biomass in the methanegenis tank 1 reactors to improve retention and reduce volume required for the methanogenesis tank;
(b)(iii) transferring biogas from the methanogenesis tank 1 through a foam trap to trap residual foam and separate it from the biogas; and
(c) collecting the biogas downstream of the foam trap.

Another embodiment provides a method of producing biogas comprising:
(a)(i) transferring an organic substrate to a hydrolysis tank;
(a)(ii) hydrolyzing the substrate in anaerobic condition in a hydrolysis tank to produce a hydrolysis liquid effluent;
(b)(i) transferring the hydrolysis effluent for a period of time 1 to a methanogenesis tank 1 comprising fixed film methanogens or granular methanogens and producing biogas and methanogenesis tank 1 liquid effluent;
wherein the hydrolysis tank and methanogenesis tank 1 each have a recirculation loop and one or more instrument detectors for monitoring one or more parameters of the liquid in the tank in the recirculation loop, and the method comprises recirculating liquid from each tank back into the same tank through the recirculation loop for that tank, and monitoring one or more parameters in each tank with the one or more instrument detectors in the recirculation loop of that tank, wherein the parameters are selected from the group consisting of pH, ORP, ionic strength, chemical oxygen demand, and dissolved methane concentration; wherein each recirculation loop has at least one valve separating the recirculation loop from its tank, and the at least one valve can be closed to allow the one or more instrument detectors to be removed for cleaning or service without allowing air to contact liquid in the tank connected to the recirculation loop.

Another embodiment provides a method of producing biogas comprising:
(a)(i) transferring an organic substrate to a hydrolysis tank;
(a)(ii) hydrolyzing the substrate in anaerobic condition in a hydrolysis tank to produce a hydrolysis liquid effluent;
(b)(i) transferring the hydrolysis liquid effluent for a period of time 1 to a methanogenesis tank 1 comprising fixed film methanogens or granular methanogens and producing biogas and methanogenesis tank 1 liquid effluent;
(b)(ii) transferring the methanogenesis tank 1 liquid effluent to a methanogenesis tank 2 comprising fixed film methanogens or granular methanogens during period of time 1 and producing biogas and methanogenesis tank 2 liquid effluent in methanogenesis tank 2;
(b)(iii) discharging methanogenesis tank 2 liquid effluent during period of time 1;
(c) and then switching the order of methanogenesis tanks 1 and 2 and
(c)(i) transferring the liquid hydrolysis effluent for a period of time 2 to said methanogenesis tank 2 and producing biogas and methanogenesis tank 2 liquid effluent in methanogenesis tank 2;
(c)(ii) transferring the methanogenesis tank 2 liquid effluent to said methanogenesis tank 1 during period of time 2 and producing biogas and methanogenesis tank 1 liquid effluent in methanogenesis tank 1;

(c)(iii) discharging methanogenesis tank 1 liquid effluent during period of time 2.

In all these methods, the liquid in the hydrolysis tank is preferably intermittently or continuously mixed. Mixing keeps any solids suspended so they can be more efficiently digested and broken down. It is also important to periodically remove undigestible solids from the hydrolysis tank. This can be accomplished by having the solids evenly suspended when effluent is removed from the hydrolysis tank.

Another embodiment provides a mobile system for digesting organic matter and producing biogas, the system comprising: a shipping container or trailer adapted for carriage on a truck or train; the shipping container or trailer containing: (a) a digester comprising: (i) a pump for pumping a liquid containing organic material into (ii) a hydrolysis tank; the hydrolysis tank hydraulically connected to (iii) a methanogenesis tank comprising fixed film methanogens and an outlet for liquid effluent; (iv) a heater adapted for heating liquid in the container or liquid fed into the hydrolysis tank or methanogenesis tank; (v) a plurality of instruments having detectors in contact with liquid or gas in the hydrolysis tank and methanogenesis tank; the instruments linked to a (b) computer for receiving data; and the computer linked to a (c) modem for transmitting data from the shipping container or trailer to a remote computer.

Another embodiment provides a method of producing biogas comprising: heating clean water to steam or hot water; mixing the steam or hot water with an organic substrate; and fermenting the organic substrate to biogas.

Heaters for anaerobic systems typically involve metal heating elements in contact with the liquid containing substrate being digested. The organic matter in anaerobic digesters, including organic solids being digested, hydrolytic microorganisms, and methanogenic microorganisms, and other biomass, all can corrode heating elements and shorten the lives of heating elements. By heating clean water to produce hot water or steam and mixing the hot water or steam with the an organic substrate to be digested, instead of heating the organic substrate directly, we have been able to extend the life of the heating element.

Another embodiment provides a method of producing biogas comprising: (a) hydrolyzing an organic substrate in anaerobic condition in a hydrolysis tank to produce a hydrolysis liquid effluent; (b) transferring the hydrolysis liquid effluent to a methanogenesis tank 1 comprising fixed film methanogens or granular methanogens and producing biogas and methanogenesis tank 1 liquid effluent; wherein the methanogenesis tank 1 has a liquid substrate and a recirculation loop for recirculating liquid substrate in the methanogenesis tank, the recirculation loop comprising a heating element in contact with liquid substrate in the recirculation loop; (c) recirculating the liquid substrate through the recirculation loop and returning the liquid substrate to remainder of the methanogenesis tank; and (d) heating the liquid substrate in the recirculation loop with the heating element; wherein the liquid substrate in the recirculation loop is depleted in the fixed film methanogens or the granular methanogens compared to liquid substrate in the remainder of the methanogenesis tank.

DETAILED DESCRIPTION

The inventors have developed new methods and systems for anaerobic digestion of organic material to biogas.

Figure 1:
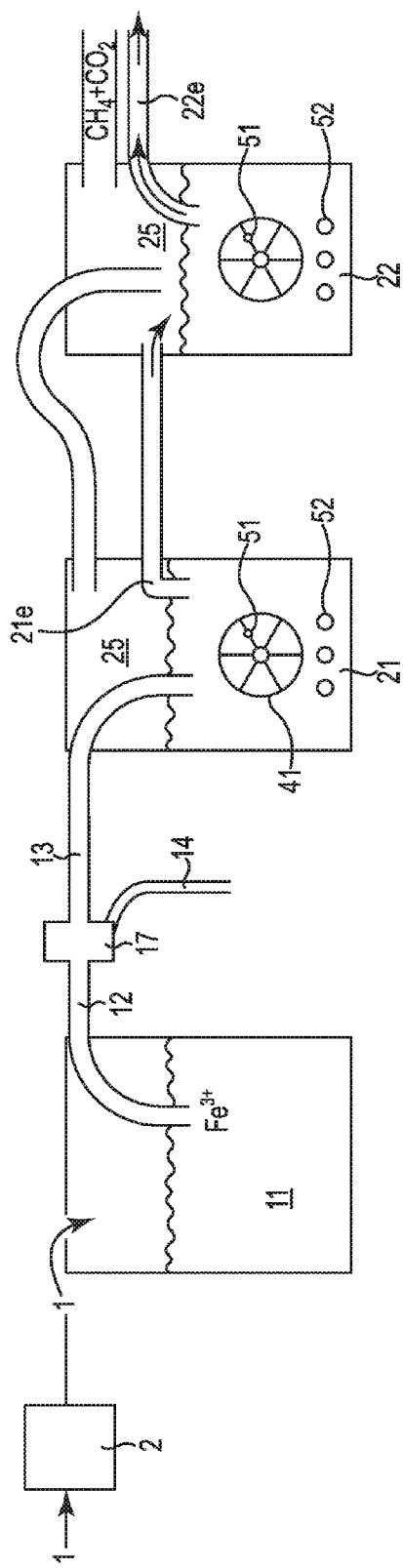
FIG. 1 shows the components of a digester system and a method of producing biogas.

One method and a system of the invention is shown in FIG. 1. It involves transferring an organic substrate 1 to a hydrolysis tank 11. The organic substrate 1 can be any suitable organic substrate. In some cases it is chemical manufacturing waste. In other embodiments, it is agricultural or food waste, for instance, potato skins, banana skins, food grease or food oil, corn stover, etc. In other embodiments it is municipal garbage, municipal waste, sewage, or livestock manure. In other embodiments, it is slaughterhouse waste. It also may be, of course, a combination of wastes, which may include these wastes or others.

In FIG. 1, the organic substrate 1, where it includes solids, may be processed by grinding in grinder 2 to produce smaller solids to enhance hydrolysis. In a specific embodiment, the organic substrate 1 is processed by grinding to a particle size of 6 mm or less. In some cases, the organic substrate is or includes solids, in others it may be or include a liquid.

The organic substrate 1 is transferred to hydrolysis tank 11, where it is hydrolyzed in anaerobic conditions. The hydrolysis tank may optionally include ferric iron ($Fe^{3+}$). The ferric iron can be in the form of magnetite or other forms of solid or dissolved ferric iron. The ferric iron is believed to improve the efficiency of anaerobic hydrolysis because it functions as an electron sink. It is believed that other metallic electron sinks (electron acceptors) could replace the ferric iron. These would include, for instance, Mn, Co, Ni, Cu, and Zn cations. In other embodiments, the hydrolysis tank does not include ferric iron or any other metallic cation electron sink.

In the hydrolysis tank the substrate is hydrolyzed and fermented to smaller molecules that are substrates for methanogenesis. The content of the hydrolysis tank is preferably intermittently or continuously mixed. A hydrolysis effluent 12 is produced and is transferred to a first methanogenesis tank 21. The hydrolysis effluent 12 is preferably processed by a solids separator 17 to separate out a solids fraction 14, which is typically removed from the system, and a screened hydrolysis effluent 13. We have found that placement of a solid separator at this stage improves the efficiency and speed of the methanogenesis stage.

The solids separator 17 in one embodiment is a screw type solids separator. Other types of solids separators may also be used.

In all the methods described herein, the liquid in the hydrolysis tank is preferably intermittently or continuously mixed. Mixing keeps any solids suspended so they can be more efficiently digested and broken down. It is also important to periodically remove undigestible solids from the hydrolysis tank. This can be accomplished by having the solids evenly suspended when effluent is removed from the hydrolysis tank. Seelction of mixing intensity, frequency, and equipment used for mixing can be optimized to effect conversion of the substrate or organic acids and other soluble organic compounds.

The screened hydrolysis effluent is transferred to methanogenesis tank 21. This is an anaerobic tank holding methanogens. Methanogens are obligate anaerobic microorganisms classified as archaea. The methanogenesis tank preferably contains a substrate 41 on which methanogens can grow to form a fixed film 51. A good substrate is JAEGER SURFPAC. The methanogenesis tank 21 may contain granular bed methanogens 52 in addition to fixed film methanogens 51 or instead of fixed film methanogens 51.

Methanogenesis tank 21 produces methanogenesis tank liquid effluent 21e.

The biogas from methanogenesis tank one (21) accumulates in a headspace 25.

Methanogenesis tank one liquid effluent 21e passes to methanogenesis tank two (22). We have found that using two methanogenesis tanks in sequence gives more complete digestion of the substrate and more complete conversion to biogas. Having a second methanogenesis tank also helps trap granules of methanogens to prevent loss of the methanogens. It helps trap the granules because the gas production is slower in the second methanogenesis tank since the substrate is depleted by the first methanogenesis tank. Less gas production means less bubbles trapped in the granules and therefore the granules are less buoyant in the second methanogenesis tank and less likely to rise and be carried out in the liquid effluent 22e.

Having recycle loops in each of the methanogenesis reactors (tanks) also serves to faver the growth of granulated and attached film biomass. Over time, poorly settling fluffy biomass is removed while heavier granules and film attached to the substrate for fixed film biomass is retained.

A liquid effluent 22e is withdrawn from the second methonagenesis tank 22 and biogas comprising $CH_4$ and $CO_2$ is also produced and collected.

The biogas in methanogenesis tank 22 also accumulates in a headspace 25 before being collected or vented.

We have found that it is beneficial to switch the order of methanogenesis tank one (21) and methonagenesis tank two (22). This improves the functioning of both tanks and improves the speed and efficiency of biogas production from the substrate. The second tank in order receives less food (substrate for methanogens), so the microorganisms would gradually die back if the tank remained in the second position permanently. By switching the order periodically, we can maintain a high biomass density in the second tank that completes the digestion of the feedstock to biogas with high yield. It also, as mentioned above helps to trap the granular bed methanogens in the second methanogenesis tank before they escape the system.

The methanogenesis tanks one and two (21 and 22) can be switched in order at fixed periods of times, for instance every 24 hours or every 12 hours. Alternatively, we have found good results by switching based on parameters that are easily measured using instruments. One such measurement is the oxidation-reduction potential (ORP) of either or both tanks. For example, the first methanogenesis tank in sequence (the lead methanogenesis tank) should have an ORP of −300 to −550 mV. The ORP in the lead methanogenesis tank rises over time, and it can be switched when the ORP in it rises to a present value. For instance, the switch may be made when the ORP in the lead methanogenesis tank rises to an ORP in the range of −300 to −400 mV. For instance, the preset value to trigger the switch may be a specific ORP between −300 and −400 mV, for instance −350 mV. The second methanogenesis tank (the lag methanogenesis tank) in sequence should have an ORP of about −300 to −550 mV. The ORP in the lag methanogenesis tank falls over time (becomes more negative). We have in some cases executed the switch when the ORP in the lag methanogenesis tank falls to an ORP in the range of −450 mV to −550 mV. When the second reactor is moved to the first position, its ORP will rise because it will begin receiving hydrolysis tank effluent, which has a higher ORP.

The specific ORP ranges listed in the foregoing description are presented for illustration purposes and may vary from feedstock to feedstock.

In a specific embodiment, the time period between switching the order the two methanogen tanks is between 6 and 24 hours inclusive. In another embodiment, it is between 6 and 48 hours, inclusive.

The hydrolysis tank 11, in addition to preferably containing $Fe^{3+}$, preferably contains a microorganism that that reduces $Fe^{3+}$ and produces at least one volatile organic acid from organic substrates. Thus, $Fe^{3+}$ is an electron acceptor for anaerobic respiration. This improves the speed and efficiency of anaerobic digestion. The microorganism that reduces $Fe^{3+}$ and produces at least one volatile organic acid from organic substrates in one embodiment is or is derived from ATCC 55339.

Figure 2:
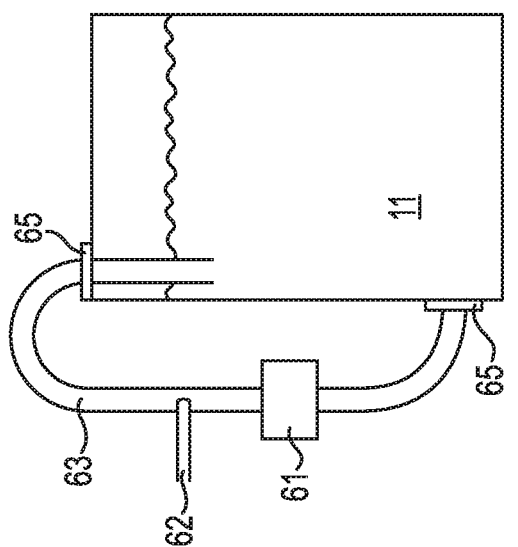
FIG. 2 shows an anaerobic digestion tank with a recirculation loop and a monitoring instrument in the loop.

Each of the tanks preferably has a recirculation loop, as shown in FIG. 2 for hydrolysis tank 11. Recirculation loop 63 allows recirculation of fluid in the tank. This is one way of maintaining an upward flow of liquid in the main portion of the tank to stir the contents of the tank and maintain good mixing and less settling. This improves the efficiency of the digestion. A recirculation pump 61 is coupled to recirculation loop 63 to pump liquid through the loop. In specific embodiments, the recirculation loop 63 includes one or more probes 62 to measure one or more parameters of the liquid in the loop, such as pH, ORP, total organic carbon, and chemical oxygen demand. The liquid in the recirculation loop 63 of course is the same liquid in the tank 11, so this allows one to measure these parameters in the tank. The recirculation loop 63 can include valves 65 that can be shut off to separate the recirculation loop. This allows us to remove the probe or probes 62 for cleaning or calibration, without emptying the entire reactor and without exposing the contents of the tank to oxygen.

Another embodiment of the invention is the use of a pressure gauge near the bottom of the tank and a gas pressure gauge in the head space of the tank to measure liquid level in the tank. By the difference between pressure in the bottom of the tank and gas pressure above the liquid level, one can calculate the height of the liquid by use of a density of 1.00 kg/L or whatever the density of the liquid in the tank actually is. Thus, another embodiment is a method of calculating height of liquid in a tank, wherein the tank comprises a liquid level and a gas headspace above the liquid level, the method comprising measuring liquid pressure at a known position A near the bottom of the tank and measuring gas pressure in a headspace above the liquid, and calculating the height of the liquid above the known position A by the difference in pressure between the gas pressure in the headspace and the liquid pressure at position A.

In yet another embodiment, one or more hydrolysis tanks and/or one or more methanogenesis tanks comprise a gas pressure probe in a headspace of the tank and a liquid pressure probe near the bottom of the tank.

The hydrolysis tank 11 and first methanogenesis tank 21 and second methanogenesis tank 22 may each comprise a plurality of vessels, although they are each shown as a single vessel in FIG. 1.

Each of the reactors—the hydrolysis reactor, the methanogenesis reactor 1 and methanogenesis reactor 2—has a hydraulic retention time, which is the average time that the liquid is contained in the reactor. This is equal to the inflow flow rate (or outflow flow rate) divided by the liquid volume of the reactor. With the systems and methods described herein, surprisingly small hydraulic retention times can be used while still achieving almost complete conversion of the substrate to biogas. In one typical embodiment, the hydrolysis tank has a hydraulic retention time of 2 days, and methanogenesis tanks 1 and 2 each have a hydraulic retention time of 1 day, and the entire system has a hydraulic retention time of 4 days.

In specific embodiments, the hydrolysis tank has a hydraulic retention time of 9 hours or less, 24-96 hours, 24-72 hours, 36-48 hours, or 72 hours or less.

In specific embodiments, methanogenesis tank 1 and methanogenesis tank 2 each have a hydraulic retention time of 48 hours or less, 12-48 hours, 24-38 hours, 12-36 hours, 24-36 hours, or 12-24 hours.

The total hydraulic retention time is the hydraulic retention time for the whole system, i.e., the sum of the hydraulic retention times of all hydrolysis tanks and methanogenesis tanks connected in series. In specific embodiments, the total hydraulic retention time is 8 days or less, 6 days or less, 4 days or less, about 4 days, 3-6 days, 4-8 days, 3-8 days, or 2-8 days.

Figure 3:
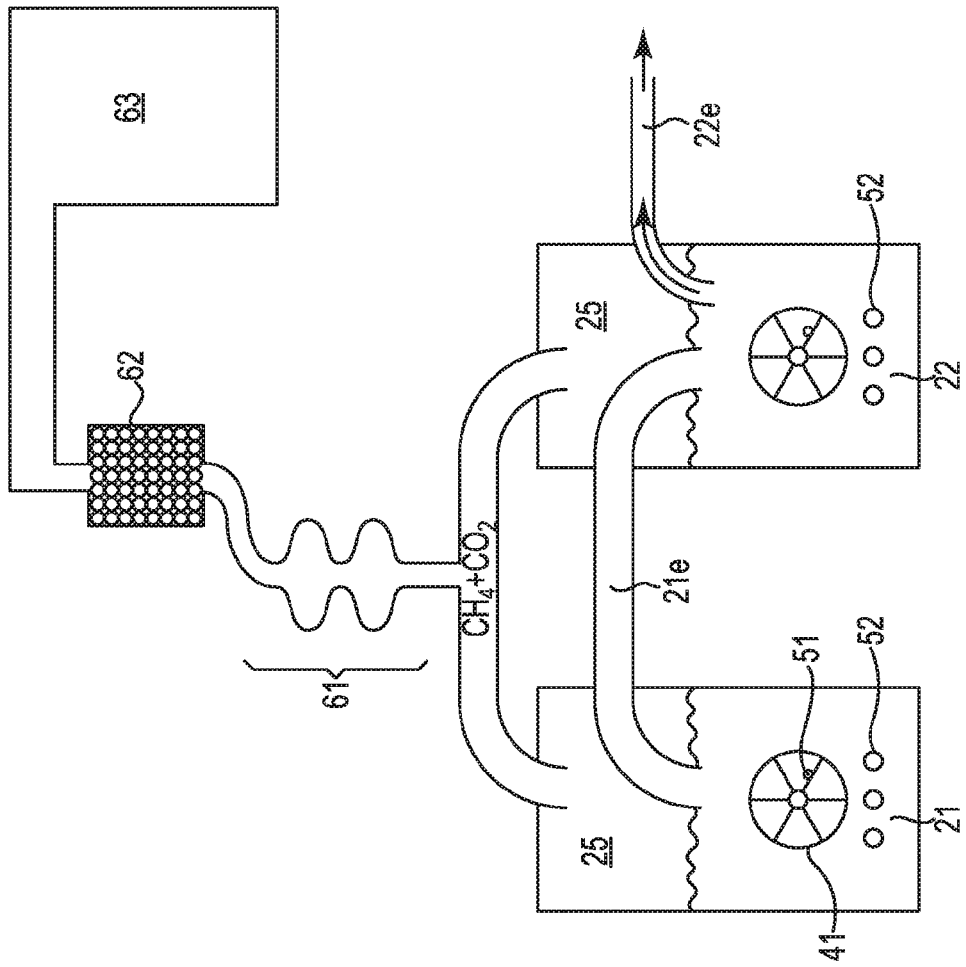
FIG. 3 shows methanogenesis tanks with a foam trap and components for collecting biogas.

Referring to FIG. 3, the biogas accumulates in headspace 25 of the one or more methanogenesis tanks 21 and 22. Where there are two or more methanogenesis tanks, the headspace of the two or more tanks is preferably connected, as shown in FIG. 3. There may be valves that can be closed to separate the tanks.

The headspace biogas in one embodiment is collected through a foam trap 62. The foam trap 62 has a large amount of surface area, on which foam and other liquids are trapped or condense.

The foam trap is advantageously used because foam can plug the gas collection system and can cause corrosion of system hardware.

Upstream from the foam trap, in some embodiments, may be a gas/solids separator 61. This also separates solids from the gas and separates a significant amount of liquids and foam from the gas as well. The gas/solids separator typically has an over-and-under flow pattern with a wide section, then a narrow passageway, then another wide section. Solids and liquids tend to be trapped and fall back down in the narrow passageway.

After the foam trap 62, the biogas is collected in biogas collector 63. This is preferably expandable to maintain the same gas pressure at all times.

In all the methods, systems, and devices described herein, the methanogens may be retained as fixed film methanogens or as granular bed methanogens. In some embodiments, both fixed film and granular bed methanogens are present.

Figure 5:
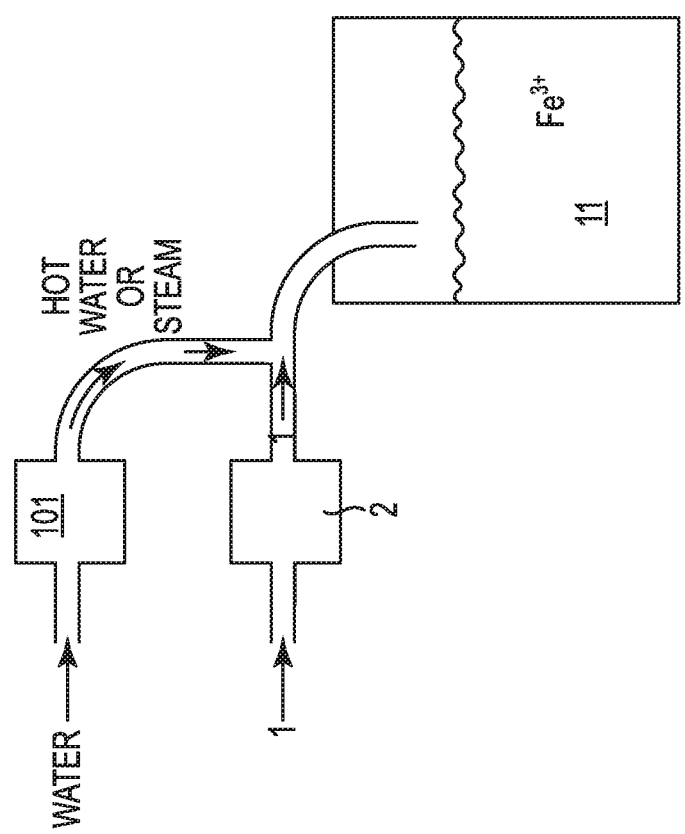
FIG. 5 shows use of a heater to heat feed water for mixing with the feed organic substrate in the hydrolysis tank.

FIG. 5 shows a system and method of the invention with hydrolysis tank 11. Organic substrate 1 is shown being added to the hydrolysis tank 11 for hydrolysis of the organic substrate 1. In FIG. 5, organic substrate 1 also passes through a grinder 2 to grind solids to smaller solids particles for better hydrolysis and digestion of the solids. In FIG. 5 a heater 101 is shown. Water is heated by the heater 101 to produce hot water or steam, and the hot water or steam is mixed with the organic substrate. The hot water or steam may be mixed with the organic substrate before it is added to the hydrolysis tank, as is shown in FIG. 5, or can be mixed with the organic substrate in the hydrolysis tank. Either method accomplishes the goal of heating the organic substrate achieve an optimal temperature to promote faster and more efficient hydrolysis. With the method shown in FIG. 5, the heating element of the heater 101 only contacts clean water, not the organic substrate. This prolongs the life of the heater. Also, it may be advantageous to premix the hot water or steam with the organic substrate before adding the organic substrate to the hydrolysis tank 11. This prevents contacting the microorganisms in the hydrolysis tank with extremely hot water or steam, which would happen if the hot water or steam is mixed directly with the contents of the hydrolysis tank, and which might kill some of the hydrolytic microorganisms. The term "clean water" in this context is intended to mean not that the water is necessarily absolutely pure, but that it has less organic matter and other substances that can damage the heating element than the remainder of the "organic substrate."

Figure 6:
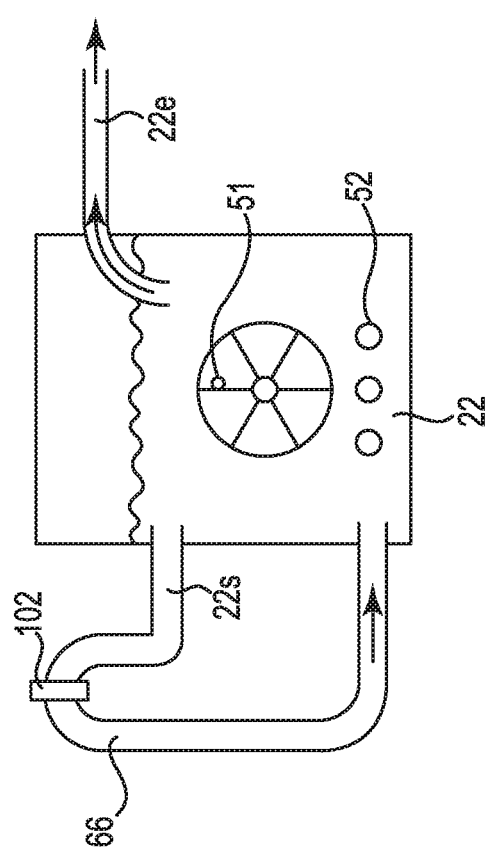
FIG. 6 shows use of a recycle flow and a heater element with a methanogenesis tank.

FIG. 6 shows the use of a heating element in a recirculation loop connected with a methanogenesis tank. In FIG. 6, methanogenesis tank 22 is shown with a recirculation loop 66. Liquid substrate 22s of the methanogenesis tank is circulated through the recirculation loop 66, and it contacts a heating element 102 in the recirculation loop 66. This allows heating of the liquid substrate 22s in the methanogenesis tank to an optimum temperature for methanogenesis. The recirculation loop 66 is shown connected to the methanogenesis tank 22 near the upper level of the liquid substrate 22s. Since the granules 52 and fixed film methanogens 51 are heavier than water, they will tend to fall in the tank and be depleted in the liquid substrate in the recirculation loop 66 as compared to the liquid substrate in the remainder of the methanogenesis tank 22. This tends to save the heating element by minimizing its contact with solids and methanogenic granules and microorganisms.

The use of a recirculation flow as is shown in FIG. 6, with or without a heating element in the recirculation loop, is beneficial. By optimizing the rate of recirculation, growth of granular methanogens is optimized while preventing washout of the granular methanogens. Too rapid a flow can lead to washout of the granular methanogens through liquid effluent 22e. But lower flow rates promote growth of granular methanogens.

Figure 4:
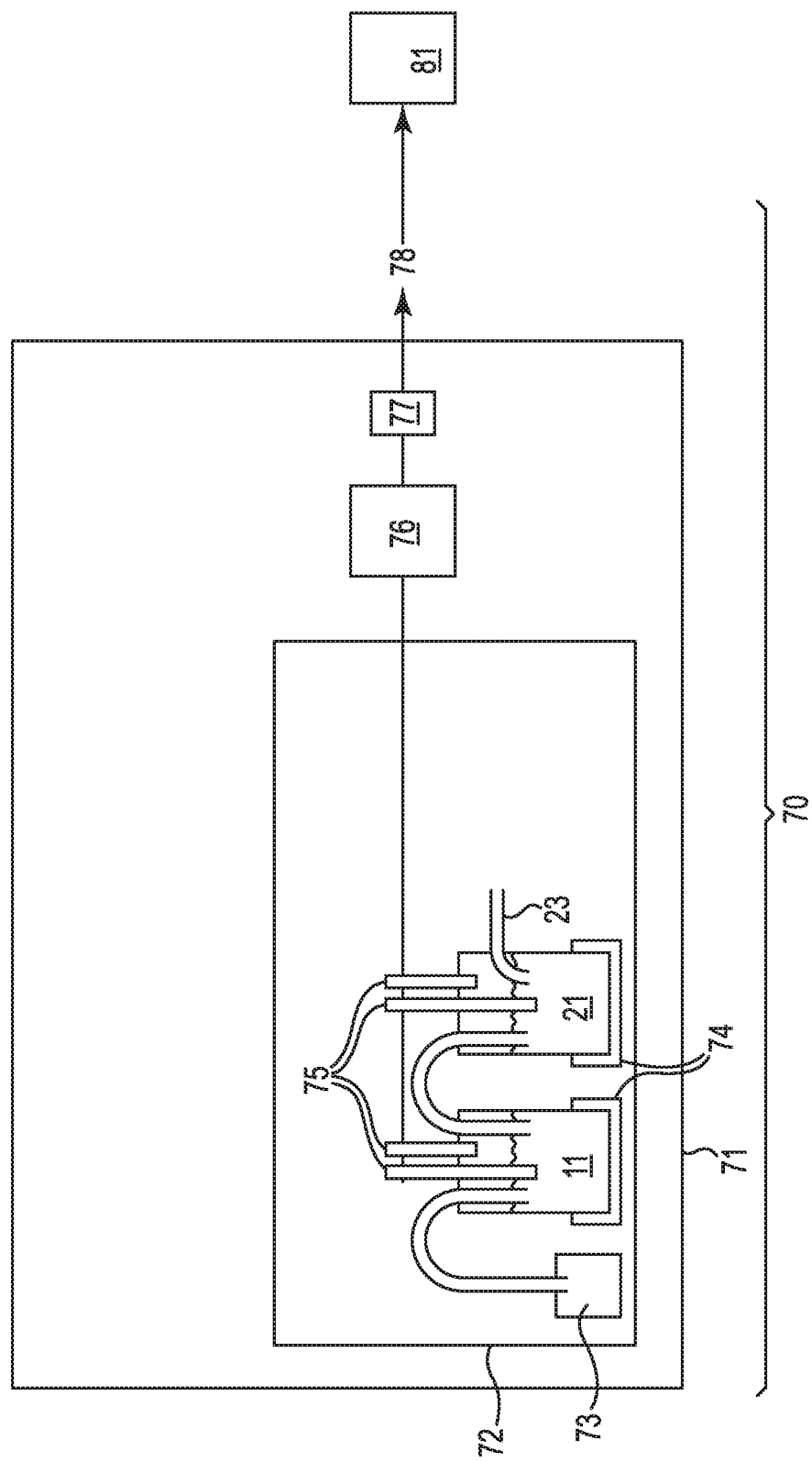
FIG. 4 shows a mobile system for digesting organic material and producing biogas. The mobile system can be shipped to a distant site and used to test and demonstrate the methods of the invention on specific substrates at distant sites, while still being controlled and monitored at a base location.

FIG. 4 shows a mobile system of the invention for digesting organic matter and producing biogas. The mobile system 70 comprises a shipping container or trailer 71 adapted for carriage on a truck or train. The shipping container or trailer contains: (a) a digester 72 comprising: (i) a pump 73 for pumping a liquid containing organic material into (ii) a hydrolysis tank 11; the hydrolysis tank 11 hydraulically connected to (iii) a methanogenesis tank 21 comprising fixed film methanogens. The methanogenesis tank comprises (iv) an outlet 23 for liquid effluent. The digester further comprises (v) a heater 74 adapted for heating liquid contained in or fed into the hydrolysis tank or methanogenesis tank; and (vi) a plurality of instruments 75 having detectors in contact with liquid or gas in the hydrolysis tank and methanogenesis tank. The instruments are linked to (b) a computer 76 for receiving data; and the computer linked to (c) a modem 77 for transmitting data 78 from the shipping container to a remote computer 81. The remote computer may be at a distance from the shipping container, that is, across the country or the world.

The remote computer and the system may be configured to allow the remote computer to control and monitor the digester.

The mobile system may also include a solids separator operating between the hydrolysis tank and the methanogenesis tank, as described above.

The mobile system allows the digester system to be transported by truck or rail to a distant site to test and demonstrate the performance of the system on a particular feedstock on location and under the conditions found at the location. The digester can be remotely monitored and controlled by persons at a distance so that those persons do not need to travel also to the site where the system is tested.

EXAMPLE

The Novus Bio-Catalytic (NBC™) mobile pilot is a trailer-mounted, multi-cell, two stage anaerobic digestion system. The system currently consists of 3 digestion cells, but has been designed to accommodate up to 7 cells. Each digestion cell is 4 feet in diameter (O.D.) and 9 feet tall with a liquid capacity of 3,000 gallons (8' liquid column) and a gas headspace of 50.3 cubic ft. In the 3 cell configuration, liquid capacity is 9,000 gallons. The pilot is housed in a semi-trailer with a 50'×7' box, ventilated and with electric baseboard heating. The pilot is designed to digest a variety of solid and liquid organic substrates. In the current 3 cell configuration, the digestion loading capacity of the system is:

1. Solids capacity: 1000 lbs (dry wt.) per day
2. Liquid Capacity: 500 gallons per day The pilot system consists of the following:

1. Subsystem 1000: Feed Preparation and Pumping
2. Subsystem 2000: Hydrolysis
3. Subsystem 3000: Solids separation and recycle
4. Subsystem 4000: Methanogenesis and Polishing
5. Subsystem 5000: Gas Handling The stages and their modes of operation are described in the following sections.

Subsystem 1000: Feedstock Preparation and Mixing

The purpose of Subsystem 1000 is to convert solid and liquid substrate to a slurry suitable for hydrolytic digestion. The subsystem blends solid and liquid substrates with magnetite into a slurry, reducing the particulate size of the solid substrate so that it can pass through a ¼" opening and blend it with liquid waste and magnetite additive into a slurry. Stage Subsystem 1000 components include a feed pump (P1000) followed by a grinder with an open feed hopper for inlet.loop Subsystem 1000 includes a influent pump to the grinder (40 gpm capacity), a feed water heater (A.O. Smith model ATI 305201, 175,000 Btu/hour capacity), and a feed pump to the hydrolysis tank, and a feed make-up water tank, for water to add to the hydrolysis tank as needed.

Subsystem 2000: Hydrolysis

Subsystem 2000 solubilizes the solid particulate in the slurry to liquid organic acids (hereinafter referred to as leachate) through the biochemical and bacteriological catalysis of water and complex molecules (hydrolysis). The slurry is mixed and digested under anaerobic conditions at 35° C. to facilitate the converting the solids into volatile acids. Feedstock slurry is pumped via P1000 into hydrolysis tank TK2001, while leachate/slurry is pumped out of the tank via another pump. The hydrolysis tank (Ace Roto Mold VT1000-64, 1000 gallons). The contents in the hydrolysis tank are mixed by a ½ hp mixer with a variable motor. A discharge pump withdraws slurry from the top of the tank. Digestion parameters—[pH, ORP and Temperature]—are monitored by instrument probes mounted in the recirculation pipe. Liquid level in the tank is monitored through a pressure element PE2001, set to maintain the preset level. In addition, a high level alarm LAH 2001 shut down the pumps P1000. The pumps are then restarted only after intervention and reset by the operator.

Parameters monitored in Subsystem 2000 are:

| Control Input | Output | Type of output | Parameter Measured |
|---|---|---|---|
| AIT 2001.1 | Pump P2000 On/Off signal | Digital | pH |
| AIT 2001.1 | Pump P2000 RPM | Digital | pH |
| PE2001 | Cut off signal to P1000 | Digital | Tank Level |
| LSH 2001/PE2001 | High Level Alarm LAH | Digital | Tank Level |
| PE2001 | Cut off signal to P1000, | Digital | Tank Level |
| Temperature TIT2001 | Thermostat Control Signal | Digital | Reactor Temperature |
| AIT 2001.2 | Record ORP | Digital | Reactor ORP |

Subsystem 3000: Solids Separation and Recycle

Subsystem 3000 consists of the solids separation and leachate recycle systems. The liquefied slurry from the hydrolysis tank is pumped to the Solids Separator (Vincent Corp. Model KP-10, 10 gpm capacity) using the Centrifugal Pump (American Machine Tool, AMPT-315-95A, 40 gpm capacity). Liquid leachate from the Separator is pumped to Methanogenesis Subsystem 4000 on a continuous basis.

Subsystem 4000: Methanogenesis

Subsystem 4000 converts the leachate produced in Subsystem 2000 (Hydrolysis) into biogas. The clarified leachate from the solids separator is collected by gravity into tank TK-4000 that serves as a feed pump station for this Subsystem. The leachate is pumped by pumps P-4000.a or 4000.b The pump P-4000.a is oversized to keep the tank TK4000 mixed. TK4000 will have 2 chambers connected by an open loop at the bottom. A portion of the flow will be directed into TK4001 or TK4002 and P4000.b is a variable speed low flow pump. The leachate is passed though loose fill media under strict anaerobic conditions at 35° C. to facilitate the conversion of the acids into biogas. Leachate is pumped into the tank at the bottom and is removed at the top of the tank by gravity. TK4001 (methanogenesis tank 1) is mixed via recycle pump P4001, while TK4002 (methanogenesis tank 2) is mixed using pump P4002.

Both pumps withdraw leachate from the top and re-inject it at the bottom of their respective tanks. Digestion parameters—[pH, ORP and Temperature]—are monitored by instrument probes mounted on the discharge loop of pumps P4001 and P4002.

Liquid level in the tanks is monitored through Pressure elements PE4001 and P4002, set to maintain levels of 8' in the tank, +/−3," by matching the rate of inflow and outflow: flow into the bottom of the tank via pump P4001, (and/or P4002) and 3 gph flow out at the top of TK4001 (and/or TK4002) Outflow is determined by a gravity feed past a pre-set constricted opening. As the liquid levels in TK4001 (and/or TK4002) rise to or drop below the preset levels as signaled by level sensor PE4001 (or PE4002), the system starts or stops the pumps P4000_B and P5000 in order to bring the liquid level back within range.

In addition, a high levels alarms LAH 4001 and LAH 4002 and a low level alarm LAL 4000 in respective tanks TK4001 and TK4002 will shut down pumps P4000_B, and P5000 in the event the pre-set maximum or minimum levels (in TK4000, TK4001 or in TK4002 is reached. The pumps will be restarted when the levels change.

Tanks TK4001 and TK4002 are designed to function in a series configuration wherein the lead and lag positions are switched periodically to achieve higher removal efficiencies and maintain more robust bacteria colonies in both tanks. The switching is determined by the ORP level in the lead tank.

The switching of the flow order of tanks TK4001 and TK4002 is accomplished by controlling valves V4000.5, V4000.6, V4001.10 and V4001.26. The valve configurations for the two flow arrangements are as follows:

| Flow Regime | Valve 4000.5 | Valve 4000.6 | Valve 4001.26 | Valve 4001.1026 |
|---|---|---|---|---|
| TK4001-TK4002 | Open | Open | Closed | Closed |
| TK4002-TK4001 | Closed | Closed | Open | Open |

Parameters monitored in Subsystem 4000 are:

| Control Input | Output | Type of output |
|---|---|---|
| AIT 4000.1 | Pump P4000.1 Status | Digital |
| LSH 4000 | High pump level alarm | Digital |
| Temperature TIT4001.1 | Thermostat Control Signal | Digital |
| pH, AIT 4001.2 | Low pH alarm & Pump Speed Control Signal for pH below limits | Digital |
| ORP, AIT 4001.3 | High ORP signal to reverse flows | Digital |
| PE4001 | Start and stop signal to P4000_A and P4000_B | Digital |
| LSH 4001/PE4001 | High Level Alarm LAH | Digital |
| PE4002 | Cut off signal to P4001 | Digital |
| LSH 4002/PE4002 | Low Level Alarm LAL | Digital |
| PE4002 | Cut off signal to P4002 | Digital |
| LSH 4002/PE4002 | High Level Alarm LAH | Digital |
| PE4002 | Cut off signal to P4002, Close Valve ( ) | Digital |
| LSH 4002/PE4002 | Low Level Alarm LAL | Digital |
| pH, AIT 4002.2 | Low pH alarm & Pump Speed Control Signal for pH below limits | Digital |
| ORP, AIT 4002.3 | High ORP signal to reverse flows | Digital |
| Temperature TIT4002.1 | Thermostat Control Signal | Digital |
| pH, AIT 4002.2 | Low pH alarm & Pump Speed Control Signal for pH below limits | Digital |
| ORP, AIT 4002.3 | High ORP signal to reverse flows | Digital |
| FE4000 | Flow Signal | Digital |

Subsystem 5000: Gas Handling

The gas produced is measured and recorded on a continuous basis. In addition the system has an ambient gas level monitor mounted inside the trailer outside the tanks for safety purposes. The trailer is equipped with a large manometer consisting of 2 gas holding and 2 water balancing tanks to maintain positive pressure on the system as well as allow the tanks to be filled and emptied without introducing air. In essence the manometer functions like a floating cover.

What is claimed is:

1. A method of producing biogas comprising:
   (a) hydrolyzing an organic substrate in anaerobic condition in a hydrolysis tank to produce a hydrolysis liquid effluent;
   (b) transferring the hydrolysis liquid effluent to a methanogenesis tank 1 comprising fixed film methanogens or granular methanogens and producing biogas and methanogenesis tank 1 liquid effluent;
   wherein the methanogenesis tank 1 has a liquid substrate and a recirculation loop for recirculating liquid substrate in the methanogenesis tank, the recirculation loop comprising a heating element in contact with liquid substrate in the recirculation loop;
   (c) recirculating the liquid substrate through the recirculation loop and returning the liquid substrate to remainder of the methanogenesis tank; and
   (d) heating the liquid substrate in the recirculation loop with the heating element;
   wherein the liquid substrate in the recirculation loop is depleted in the fixed film methanogens or the granular methanogens compared to liquid substrate in the remainder of the methanogenesis tank.

2. The method of claim 1 wherein the methanogenesis tank comprises granular methanogens fixed film methanogens and the liquid substrate in the recirculation loop is depleted in the granular methanogens compared to the liquid substrate in the remainder of the methanogenesis tank.

3. The method of claim 1 wherein step (b) comprises separating solids from the hydrolysis liquid effluent to produce a solids fraction and a screened hydrolysis effluent, and transferring the screened hydrolysis effluent to the methanogenesis tank.

4. The method of claim 1 wherein the step (d) comprises heating clean water to steam or hot water; and mixing the steam or hot water with an organic substrate to heat the organic substrate.

5. The method of claim 1 wherein step (a) comprises:
   (a)(i) grinding an organic substrate comprising solids to produce smaller solids particles;
   (a)(ii) transferring the substrate with smaller solids particles to a hydrolysis tank;
   (a)(iii) hydrolyzing the substrate in anaerobic condition in the hydrolysis tank;
   (a)(iv) transferring effluent from the hydrolysis tank to a solids separator; and
   (a)(v) separating solids from the hydrolysis effluent to produce a solids fraction and a screened hydrolysis effluent.

6. The method of claim 5 wherein the step of separating solids uses a solids separator that is a screw type solids separator.

7. The method of claim 1 wherein the step (a) comprises: hydrolyzing the substrate in anaerobic condition in a hydrolysis tank comprising $Fe^{3+}$ particles.

8. The method of claim 1 wherein the method comprises:
   (b)(1)(i) transferring the hydrolysis liquid effluent for a period of time 1 to a methanogenesis tank 1 comprising fixed film methanogens or granular methanogens and producing biogas and methanogenesis tank 1 liquid effluent;
   (b)(1)(ii) transferring the methanogenesis tank 1 liquid effluent to a methanogenesis tank 2 comprising fixed film methanogens or granular methanogens during period of time 1 and producing biogas and methanogenesis tank 2 liquid effluent in methanogenesis tank 2;
   (b)(1)(iii) discharging methanogenesis tank 2 liquid effluent during period of time 1;
   (b)(2) and then switching the order of methanogenesis tanks 1 and 2 and
   (b)(2)(i) transferring the liquid hydrolysis effluent for a period of time 2 to said methanogenesis tank 2 and producing biogas and methanogenesis tank 2 liquid effluent in methanogenesis tank 2;

(b)(2)(ii) transferring the methanogenesis tank 2 liquid effluent to said methanogenesis tank 1 during period of time 2 and producing biogas and methanogenesis tank 1 liquid effluent in methanogenesis tank 1;

(b)(2)(iii) discharging methanogenesis tank 1 liquid effluent during period of time 2;

wherein the methanogenesis tank 1 and methanogenesis tank 2 each has a liquid substrate and a recirculation loop for recirculating liquid substrate in the methanogenesis tank, the recirculation loop comprising a heating element in contact with liquid substrate in the recirculation loop;

(c) recirculating the liquid substrate through the recirculation loop and returning the liquid substrate to remainder of the methanogenesis tank; and (d) heating the liquid substrate in the recirculation loop with the heating element;

wherein the liquid substrate in the recirculation loop is depleted in the fixed film methanogens or the granular methanogens compared to liquid substrate in the remainder of the methanogenesis tank.

9. The method of claim 8 further comprising:

(d) switching the order of methanogenesis tanks 1 and 2 and repeating steps (b)(i), (b)(ii), and (b)(iii).

10. The method of claim 8 wherein the period of time 1 and the period of time 2 are each between 6 and 24 hours inclusive.

11. The method of claim 8 wherein the methanogenesis tank 1 and the methanogenesis tank 2 each have a hydraulic retention time of 48 hours or less.

12. The method of claim 8 further comprising monitoring oxidization-reduction potential (ORP) in methanagenesis tank 1 and/or methanogenesis tank 2, wherein the methanogenesis tank receiving the hydrolysis effluent is the lead methanogenesis tank, and the other methanogenesis tank, receiving methanogenesis tank liquid effluent from the lead methanogenesis tank, is the lag methanogenesis tank, wherein the switching step (b)(2) occurs when the ORP in the lead methanogenesis tank rises to a preset value or the ORP in the lag methanogenesis tank falls to a preset value.

13. The method of claim 12 wherein the switching step (b)(2) occurs when the ORP in the lead methanogenesis tank rises to a preset value between about −400 and −300 mV or the ORP in the lag methanogenesis tank falls to a preset value between about −450 and −550 mV.

14. The method of claim 8 wherein time period 1 and time period 2 are preset time periods.

15. The method of claim 8 wherein the sum of the hydraulic retention times for the hydrolysis tank and methanogenesis tank 1 and methanogenesis tank 2 is a total hydraulic retention time, and wherein the total hydraulic retention time is 8 days or less.

16. The method of claim 1 wherein the hydrolysis tank has a hydraulic retention time of 96 hours or less.

17. The method of claim 1 further comprising:

passing the biogas produced in methanogenesis tank 1 through a foam trap to trap foam and separate it from the biogas; and collecting the biogas downstream of the foam trap.

\* \* \* \* \*